United States Patent
Lacorte et al.

(10) Patent No.: US 11,813,290 B2
(45) Date of Patent: *Nov. 14, 2023

(54) SOLID COMPOSITIONS BASED ON MINERALS AND ORALLY DISINTEGRATING FORMULATIONS CONTAINING THE SAME

(71) Applicant: ALESCO S.R.L., Pisa (IT)

(72) Inventors: Andrea Lacorte, Pisa (IT); Germano Tarantino, Pisa (IT); Gianni Lazzarini, Agugliaro (IT)

(73) Assignee: ALESCO S.R.L., Pisa (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/024,709

(22) PCT Filed: Sep. 9, 2014

(86) PCT No.: PCT/IB2014/001780
§ 371 (c)(1),
(2) Date: Mar. 24, 2016

(87) PCT Pub. No.: WO2015/033216
PCT Pub. Date: Mar. 12, 2015

(65) Prior Publication Data
US 2016/0287633 A1    Oct. 6, 2016

(30) Foreign Application Priority Data

Sep. 9, 2013  (IT) .......................... MI2013A001483

(51) Int. Cl.
| | |
|---|---|
| *A61K 33/42* | (2006.01) |
| *A23L 33/16* | (2016.01) |
| *A61K 33/26* | (2006.01) |
| *A61K 45/06* | (2006.01) |
| *A61K 33/18* | (2006.01) |
| *A61K 33/06* | (2006.01) |
| *A61K 9/20* | (2006.01) |
| *A61K 9/14* | (2006.01) |

(52) U.S. Cl.
CPC .............. *A61K 33/42* (2013.01); *A23L 33/16* (2016.08); *A61K 9/145* (2013.01); *A61K 9/2013* (2013.01); *A61K 9/2018* (2013.01); *A61K 33/06* (2013.01); *A61K 33/18* (2013.01); *A61K 33/26* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 6,074,675 | A * | 6/2000 | Nanbu | A21D 2/02 |
| | | | | 426/74 |
| 6,495,177 | B1 * | 12/2002 | deVries | A23L 33/16 |
| | | | | 424/439 |
| 6,818,228 | B1 | 11/2004 | Walsdorf et al. | |
| 2005/0222079 | A1 * | 10/2005 | Goerne | A61K 31/4415 |
| | | | | 514/52 |
| 2007/0148259 | A1 | 6/2007 | Gupta | |
| 2008/0312168 | A1 * | 12/2008 | Pilgaonkar | A61K 9/1635 |
| | | | | 514/29 |
| 2010/0008865 | A1 | 1/2010 | Fayet et al. | |
| 2012/0288531 | A1 | 11/2012 | Tuvia et al. | |
| 2015/0250885 | A1 * | 9/2015 | Lacorte | A61K 33/42 |
| | | | | 424/489 |

FOREIGN PATENT DOCUMENTS

| | | |
|---|---|---|
| WO | 97/48392 A1 | 12/1997 |
| WO | 2005/082167 A1 | 9/2005 |
| WO | 2014009805 A1 | 1/2014 |
| WO | 2014009806 A1 | 1/2014 |

OTHER PUBLICATIONS

Best@buchi information Bulletin for Mini Spray Dryer B-290 (No. 52/2008) (2008).*
"Amended Final Report on the Safety Assessment of *Oryza sativa* (Rice) Bran Oil, *Oryza sativa* (Rice) Germ Oil, Rice Bran Acid, *Oryza sativa* (Rice) Bran Wax, Hydrogenated Rice Bran Wax, *Oryza sativa* (Rice) Bran Extract, *Oryza sativa* (Rice) Extract, *Oryza sativa* (Rice) Germ Powder, *Oryza sativa* (Rice) Starch, *Oryza sativa* (Rice) Bran, Hydrolyyzed Rice Bran Extract Hydrolyzed Rice Bran Protein, Hydrolyzed Rice Extract, and Hydrolyzed Rice Protein", International Journal of Toxicology, vol. 25 (Suppl. 2), 2006, pp. 91-120.

* cited by examiner

*Primary Examiner* — Patricia Duffy
*Assistant Examiner* — Garen Gotfredson
(74) *Attorney, Agent, or Firm* — Pearne & Gordon LLP

(57) ABSTRACT

The present invention relates to solid compositions, preferably in powder or granule form, based on minerals (semi-finished or raw material) and a process for preparing said solid compositions. Furthermore, the present invention relates to solid formulations (final products) and orally disintegrating formulations (final products) containing said solid compositions. Moreover, the present invention relates to a process for preparing said solid formulations and said orally disintegrating formulations. Finally, the present invention relates to the use of said solid compositions or said solid or orally disintegrating formulations in the treatment of disorders or diseases related to or derived from a deficiency of minerals such as magnesium (II), calcium (II), iron (III), zinc (II) and/or iodine. All the compositions or formulations of the present invention are suitable for pediatric subjects, adolescents, athletes, men, women, pregnant women and elderly.

29 Claims, No Drawings

SOLID COMPOSITIONS BASED ON MINERALS AND ORALLY DISINTEGRATING FORMULATIONS CONTAINING THE SAME

The present invention relates to solid compositions, preferably in powder or granule form, based on minerals (semi-finished or raw material) and a process for preparing said solid compositions. Furthermore, the present invention relates to solid formulations (final products) and orally disintegrating formulations (final products) containing said solid compositions. Moreover, the present invention relates to a process for preparing said solid formulations and said orally disintegrating formulations. Finally, the present invention relates to the use of said solid compositions or said solid or orally disintegrating formulations in the treatment of disorders or diseases related to or derived from a deficiency of minerals such as magnesium (II), calcium (II), iron (III), zinc (II) and/or iodine. All the compositions or formulations of the present invention are suitable for pediatric subjects, adolescents, athletes, men, women, pregnant women and elderly.

Solid compositions based on minerals such as for example magnesium, calcium and iron (semi-finished or raw material) are known to be commercially available, which are used for preparing solid formulations (final products) for human use.

However, the solid compositions and formulations containing said solid composition based on minerals, suitable for oral route (per os) have limits and contraindications which, at times, restrict the use thereof.

A first limit is that solid, orally disintegrating formulations based on minerals such as for example magnesium, calcium, iron, zinc, iodine and mixtures thereof are commercially unavailable.

A second limit is that oral solid formulations presently marketed often contain the mineral, for example iron or magnesium or zinc, in a chemical form resulting hardly or poorly absorbable by the body and, thus, not bioavailable for the body. In some cases, in order to avoid a further reduction of the absorption in the organism, compositions based on minerals have to be administered between meals. In this event the oral administration between meals of said minerals could lead to further drawbacks.

A third drawback is that the solid compositions or formulations containing said solid compositions are poor processable from an industrial point of view, since they suffer from external conditions and, at times, tend to pack and not flow causing problems of mineral titer reproducibility and can lead to granulometric changes, the manufacturing of the formulations as final products is thereby jeopardized.

The above-cited limits/drawbacks represent only some of those most commonly and recurrently found in solid compositions based on minerals and formulations containing said compositions commercially available.

The above-mentioned limits and drawbacks are considered to depend on how the solid compositions based on minerals are prepared, the addition order of the individual components being used in the manufacturing process and the adopted operating conditions.

From the above, it is understood that the selection of the operating conditions of the process being used for preparing the solid compositions or formulations plays a pivotal role.

It would be optimal to have formulations based on minerals in which the mineral, as mineral salt, is highly bioavailable and at the same time formulations are devoid of any limits or drawbacks from the organoleptic point of view (taste, smell, color, long-term stability). Furthermore, it would be desirable to have solid or orally disintegrating formulations (final products) devoid of limits and drawbacks related to, for example, their hygroscopicity, particle agglomeration, color changing and their solubility.

Therefore, there is yet a need for having solid compositions based on minerals (semi-finished or raw material) such as for example magnesium (II), calcium (II), iron (III), zinc (II), iodine and mixtures thereof devoid of the limits and contraindications still existing in the presently marketed compositions. Moreover, there is yet a need for having solid and orally disintegrating formulations (final products) containing said solid compositions. In addition, there is yet a need for having a process for preparing said solid formulations (final products) and said orally disintegrating formulations (final products). There is also a need to have a process for preparing a solid composition based on minerals such as for example magnesium, calcium, iron, zinc and/or iodine wherein said minerals, existing as mineral salts, are made efficiently absorbable and bioavailable; said process being able to prepare a solid composition based on minerals which, upon formulation as final product is well-tolerable so that it can be administered, even under fasting conditions, to all the subject categories including pregnant women, has a good palatability and is stable over the time from the chemical-physical and organoleptic point of views, namely it is devoid of color, smell, flavor and taste changes.

The aim of the present invention is to provide solid compositions (semi-finished or raw material) based on minerals such as for example magnesium, calcium, iron, zinc, iodine and mixtures thereof in which said minerals, in the form of mineral salts, are made efficiently absorbable and bioavailable and are well-tolerated by the body in order to be administered, upon formulation in solid form and orally disintegrating form as final products, to pediatric subjects, adolescents, athletes, men, women, pregnant women and elderly, even under fasting conditions. Said solid and orally disintegrating formulations, containing said solid compositions based on minerals, have a good palatability and are stable over the time from the chemical-physical and organoleptic point of views since they do not give rise to color, smell, flavor, taste and solubility changes.

It is an object of the present invention solid compositions (semi-finished or raw materials) based on minerals such as magnesium (II), calcium (II), iron (III), zinc (II), iodine and mixtures thereof, having the characteristics as disclosed in the appended claims.

It is an object of the present invention a process for preparing said solid compositions, having the characteristics as disclosed in the appended claims.

It is an object of the present invention solid formulations (final products) as powder, granules or agglomerates containing said solid compositions, having the characteristics as disclosed in the appended claims.

It is an object of the present invention solid, orally disintegrating formulations (final products) containing said solid compositions, having the characteristics as disclosed in the appended claims.

It is an object of the present invention a process for preparing said solid formulations (final products) as powder, granules and agglomerates, having the characteristics as disclosed in the appended claims.

It is an object of the present invention a process for preparing said solid, orally disintegrating formulations (final products) having the characteristics as disclosed in the appended claims.

It is an object of the present invention the use of said solid and solid, orally disintegrating formulations in the treatment of disorders or diseases related to or derived from a deficiency of minerals such as for example magnesium, calcium, iron, zinc and/or iodine. All the formulations of the present invention are suitable for pediatric subjects, adolescents, athletes, men, women, pregnant women and elderly.

Preferred embodiments of the present invention are disclosed in the following detailed description.

The solid composition (semi-finished or raw material) based on minerals of the present invention is a composition which could exist in the form of granules or powder or aggregates having varying sizes and granulometry depending on the pharmaceutical form of the intended final formulation.

Said compositions of the present invention, at solid state in the form of granules or powders or aggregates, have a bulk density (measured by equipment and methods known to the skilled in the field) comprised from 0.2 to 0.9 g/ml, preferably from 0.4 to 0.8 g/ml.

The solid compositions based on minerals of the present invention comprise minerals selected from the group comprising or, alternatively, consisting of magnesium, calcium, iron, zinc and iodine or mixtures thereof. Minerals (or metal cations) are in the form of mineral salts.

In an embodiment, the mineral or cation magnesium (II) is in said compositions as mineral salt magnesium oxide or, alternatively, as mineral salt magnesium hydroxide; the mineral or cation calcium Ca (II) is in said compositions as mineral salt tricalcium phosphate E341; the mineral or cation iron (III) is in said compositions as mineral salt iron pyrophosphate; the mineral or cation zinc (II) is in said compositions as mineral salt zinc oxide; the mineral iodine is in said compositions as mineral salt sodium iodate; or alternatively said compositions may contain a mixture (two or three or four or five minerals) of said minerals.

In an embodiment, the solid compositions (semi-finished or raw material) based on minerals of the present invention further comprise, besides one or more of the above-cited minerals in the form of mineral salt, a sucrester and a lecithin and also, preferably, a pregelatinized starch to obtain solid compositions as granules or powders or agglomerates (semi-finished or raw material).

In another embodiment, the compositions of the present invention can be in liquid form. The liquid compositions (semi-finished or raw material) based on minerals such as magnesium, calcium, iron, zinc, iodine or mixtures thereof of the present invention further comprise, besides one or more of the above-cited minerals in the form of mineral salt, a sucrester and a lecithin and also, preferably, a guar gum and water to form liquid compositions (semi-finished or raw material).

The solid compositions (semi-finished or raw material) as granules or powder or agglomerates are then formulated with pharmacologically acceptable additives and excipients to obtain solid formulations (final products) such as for example a supplement product, a medical device or a pharmaceutical composition in the form of granules or powder or agglomerates, having a pharmaceutical form such as, for example packet, tablet, pastille or capsule.

Advantageously, the compositions as granules or powder or agglomerates (semi-finished or raw material) are formulated with pharmacologically acceptable additives and excipients to obtain orally disintegrating formulations (final products) such as for example a supplement product, a medical device or a pharmaceutical composition in the form of an orally disintegrating powder, said formulations having a pharmaceutical form of packet or stick.

Therefore, the solid compositions (semi-finished or raw material) as granules or powder or agglomerates are then formulated with sorbitol in an amount comprised from 40 to 90% by weight, preferably from 50 to 80% by weight, with maltodextrins in an amount comprised from 5 to 25% by weight, preferably from 9 to 20% by weight and citric acid in an amount comprised from 0.1 to 1% by weight and other pharmacologically acceptable additives and excipients for obtaining a final product (a supplement product, a medical device or a pharmaceutical composition) in the form of orally disintegrating granules or powder or agglomerates, preferably as orally disintegrating granules, having a pharmaceutical form such as, for example a packet or stick.

The tablets being obtained can have various shapes among those known in the pharmaceutical form field, such as for example a cylindrical or spheroidal shape. Tablets may have a weight comprised from 200 to 2000 mg. For example, a gel capsule may have a weight of 500 mg, a hard tablet may have a weight comprised from 800 to 1000 mg, whereas a chewable tablet may have a weight comprised from 1000 to 2000 mg. Capsules may consist of hard gelatin or soft gelatin or soft gel. Tablets can be coated or filmed with one or more coating layers or films capable to pass through the gastric barrier. The coating is prepared by using a beeswax solution or a sugar-based solution.

The solid compositions (semi-finished or raw material) of the present invention comprise at least a mineral selected from the group comprising or, alternatively, consisting of magnesium, calcium, iron, zinc and iodine or mixtures thereof in an amount comprised from 30 to 70%, preferably from 40 to 60%, even more preferably from 50 to 55% by weight.

In an embodiment, the iron pyrophosphate being used $\{[Fe_4(P_2O_7)_3xH_2O]$, CAS 10058-44-3, dry molecular weight 745.22$\}$ is preferably in micronized form and has an iron content comprised from 18 to 24%, preferably from 20 to 22% by weight.

The solid compositions (semi-finished or raw material) of the present invention further comprise, combined with at least a mineral, a lecithin.

Lecithin is a food additive—E322 (Directive 95/2/EC of 20.2.95 published on O.J. L61 of 18.3.95). Lecithin, due to its chemical-physical properties, primarily plays an emulsifying function and, being also rich in natural antioxidant substances, has a secondary antioxidant function as well. Directive 2008/84/EC of 27 Aug. 2008 (published on European Community O.J. No. L253 establishes the purity criteria that lecithin has to meet in order to be considered of food grade quality (E322): Acetone-insoluble (essentially the lecithin active part): 60% min.; Humidity: 2% max.; Acid number: 35 max.; Peroxide value: 10 max.; Toluene-insoluble (essentially impurities): 0.3% max.

From the chemical point of view, lecithin is a mixture of phosphoric acid, choline, fatty acids, glycerol, glycolipids, triglycerides and phospholipids. Phospholipids represent the main components thereof; they are derived from the triglyceride structure, wherein a fatty acid is replaced by a phosphate group, which confers a negative charge, and thus, polarity to the molecule; said molecule has the generic name of phosphatide. A more complex organic molecule, usually serine, choline, ethanolamine, inositol or a single hydrogen atom is bound through an ester bond to the phosphate group, giving rise to a phospholipid named phosphatidylserine, phosphatidylcholine, phosphatidylethanolamine, phosphatidylinositol or phosphatidic acid, respectively. In a more strict sense of lecithin, phosphatidylcholine is often designated. Phospholipids are characterized by a polar, water-soluble head, well-dissolving in water, whereas the two saturated fatty acids represent the two non polar, not water-soluble but lipophilic tails. Such a kind of molecules is called amphipathic and in the presence of water and fat they arrange themselves between the fatty and water molecules emulsifying them. Lecithin is a natural emulsifier.

All the solid compositions of the present invention are for oral use and do not contain neither a hydrolyzed lecithin nor an enzymatically hydrolyzed lecithin.

The lecithin being used is a powdery non-hydrolyzed lecithin and can be selected from sunflower or maize or soya lecithin. The lecithin being used is a powdery lecithin having a water content comprised from 1.5 to 4.5%, preferably from 2 to 4%, even more preferably from 2.5 to 3.5%. Advantageously, the lecithin being used is a powdery sunflower lecithin.

In an embodiment, the sunflower lecithin has a glucose amount comprised from 20 to 60%, preferably from 30 to 50%, for example about 45% by weight, such as in the product Lecico Sun CG 450 from Lecico GmbH Company-Germany.

A sunflower lecithin usable in the context of the present invention may have the following composition by weight (chemical-physical analysis): sunflower lecithin from 40 to 50%, carbohydrates from 40 to 50% (for example about 42%), proteins from 6 to 10%, ashes from 3 to 8%, humidity from 2 to 5% and a glidant others from 0.5 to 1.5%.

In the solid composition of the present invention, lecithin is in an amount comprised from 0.1 to 1.5%, preferably from 0.4 to 1.0%, even more preferably from 0.50 to 0.8% by weight.

The solid composition of the present invention comprises or, alternatively, consists of a magnesium (II) salt and a lecithin (neither non-hydrolyzed nor enzymatically hydrolyzed) in the above-cited amounts by weight. Advantageously, the mineral or cation magnesium (II) is magnesium oxide or, alternatively, magnesium hydroxide and lecithin is from sunflower and/or maize.

The solid composition of the present invention comprises or, alternatively, consists of a calcium (II) salt and a lecithin (neither non-hydrolyzed nor enzymatically hydrolyzed) in the above-cited amounts by weight. Advantageously, the mineral or cation calcium (II) is tricalcium phosphate E341 and lecithin is from sunflower and/or maize.

The solid composition of the present invention comprises or, alternatively, consists of an iron (III) salt and a lecithin (neither non-hydrolyzed nor enzymatically hydrolyzed) in the above-cited amounts by weight. Advantageously, the mineral or cation iron (III) is iron pyrophosphate and lecithin is from sunflower and/or maize.

The solid composition of the present invention comprises or, alternatively, consists of a zinc (II) salt and a lecithin (neither non-hydrolyzed nor enzymatically hydrolyzed) in the above-cited amounts by weight. Advantageously, the mineral or cation zinc (II) is zinc oxide and lecithin is from sunflower and/or maize.

The solid composition of the present invention comprises or, alternatively, consists of an iodine salt and a lecithin (neither non-hydrolyzed nor enzymatically hydrolyzed) in the above-cited amounts by weight. Advantageously, the mineral iodine is sodium iodate and lecithin is from sunflower and/or maize.

The solid compositions of the present invention further comprise, combined with a lecithin disclosed above, a sucrose ester or sucrester.

Sucresters are obtained by fatty acid esterification or transesterification of fatty acid methyl esters with carbohydrates, generally sucrose and other polysaccharides, for this reason they are also referred to as fatty acid sucrose esters. The chemical-physical properties of these compounds depend on the number and kind of esterified fatty acids. The abbreviation E473 means that sucresters are food additives permitted by the European Union legislation and regulated by ministerial decree (M.D. 1996). They are essentially emulsifiers and added in order to obtain a better stabilization between an aqueous phase and a fatty phase.

Sucrose esters are sucresters (E473) and used in the composition of the present invention at a HLB value of about 14-18, advantageously a HLB value of about 15 or 16, and used as emulsifiers.

In an embodiment sucrester E473 contains 70% of monoesters, being obtained by sucrose esterification with vegetable fatty acids (stearic and palmitic).

A sucrester usable in the context of the present invention may have the following composition by weight: total ester content at least 90%; free fatty acids (such as oleic acid) content not greater than 3%; free sucrose content not greater than 2%; humidity not greater than 4%; acid value not greater than 5. For example, sucrose esters SP70 from Chimab S.p.A Company—Italy.

Sucrose esters or sucresters are in the solid composition in an amount comprised from 10 to 20%, preferably from 12.5 to 18.5%, even more preferably from 16 to 18.0% by weight.

The solid compositions of the present invention do not contain a diglycerol fatty acid ester.

The solid compositions of the present invention comprise or, alternatively, consist of at least a mineral, a lecithin E322 (neither non-hydrolyzed nor enzymatically hydrolyzed) and sucrose esters or sucresters E473 in an amount by weight as specified above.

The solid composition of the present invention comprises or, alternatively, consists of a magnesium (II) salt, a lecithin (neither non-hydrolyzed nor enzymatically hydrolyzed) and sucrose esters or sucresters in the above-cited amounts by weight. Advantageously, the mineral or cation magnesium (II) is magnesium oxide or, alternatively, magnesium hydroxide, lecithin is from sunflower and/or maize and the sucrester is E473.

The solid composition of the present invention comprises or, alternatively, consists of a calcium (II) salt, a lecithin (neither non-hydrolyzed nor enzymatically hydrolyzed) and sucrose esters or sucresters in the above-cited amounts by weight. Advantageously, the mineral or cation calcium (II) is tricalcium phosphate E341, lecithin is from sunflower and/or maize and the sucrester is E473.

The solid composition of the present invention comprises or, alternatively, consists of an iron (III) salt, a lecithin (neither non-hydrolyzed nor enzymatically hydrolyzed) and sucrose esters or sucresters E473 in the above-cited amounts by weight. Advantageously, the mineral or cation iron (III) is iron pyrophosphate, lecithin is from sunflower and/or maize and the sucrester is E473.

The solid composition of the present invention comprises or, alternatively, consists of a zinc (II) salt, a lecithin (neither non-hydrolyzed nor enzymatically hydrolyzed) and sucrose esters or sucresters E473 in the above-cited amounts by weight. Advantageously, the mineral or cation zinc (II) is zinc oxide, lecithin is from sunflower and/or maize and the sucrester is E473.

The solid composition of the present invention comprises or, alternatively, consists of an iodine salt, a lecithin (neither non-hydrolyzed nor enzymatically hydrolyzed) and sucrose esters or sucresters E473 in the above-cited amounts by weight. Advantageously, the mineral iodine is sodium iodate, lecithin is from sunflower and/or maize and sucrester is E473.

In an embodiment, the solid compositions of the present invention can further comprise, combined with a lecithin and a sucrose ester or sucrester, a vegetable starch.

The vegetable starch is selected from rice (*Oryza sativa*) starches or maize starches. Advantageously, the starch is rice starch. Advantageously, the rice starch is a gelatinized or pregelatinized native rice starch. A pregelatinized rice starch usable in the context of the present invention may have the following chemical-physical characteristics: humidity not greater than 7%; protein content not greater than 1%; ash content not greater than 1%; pH (10% solution) comprised from 5.5 to 7.5, density 0.40-0.48 g/cm$^3$; minimum starch content 97% and fats not greater than 0.1%. An example of starch is given by the pregelatinized rice starch AX-FG-P from Reire Srl Company—Italy. The gelatinized or pregelatinized vegetable starch is in the solid compositions in an amount comprised from 15 to 40%, preferably from 20 to 35, even more preferably from 25 to 30 by weight.

In a preferred embodiment, the solid compositions of the present invention comprise or, alternatively, consist of at least a mineral, as mineral salt, a lecithin E322 (neither non-hydrolyzed nor enzymatically hydrolyzed), sucrose esters or sucresters E473 and a vegetable starch, in the above-cited amounts by weight. Preferably, said vegetable starch is a rice (*Oryza sativa*) starch or a pregelatinized rice (*Oryza sativa*) starch.

The solid composition of the present invention comprises or, alternatively, consists of a magnesium (II) salt, a lecithin (neither non-hydrolyzed nor enzymatically hydrolyzed), sucrose esters or sucresters in the above-cited amounts by weight. Advantageously, the mineral or cation magnesium (II) is magnesium oxide or, alternatively, magnesium hydroxide, lecithin is from sunflower and/or maize, the sucrester is E473 and the starch is a pregelatinized vegetable starch.

The solid composition of the present invention comprises or, alternatively, consists of a calcium (II) salt, a lecithin (neither non-hydrolyzed nor enzymatically hydrolyzed) and sucrose esters or sucresters in the above-cited amounts by weight. Advantageously, the mineral or cation calcium (II) is tricalcium phosphate E341, lecithin is from sunflower and/or maize, the sucrester is E473 and the starch is a pregelatinized vegetable starch.

The solid composition of the present invention comprises or, alternatively, consists of an iron (III) salt, a lecithin (neither non-hydrolyzed nor enzymatically hydrolyzed) and sucrose esters or sucresters E473 in the above-cited amounts by weight. Advantageously, the mineral or cation iron (III) is iron pyrophosphate, lecithin is from sunflower and/or maize, the sucrester is E473 and the starch is a pregelatinized vegetable starch.

The solid composition of the present invention comprises or, alternatively, consists of a zinc (II) salt, a lecithin (neither non-hydrolyzed nor enzymatically hydrolyzed) and sucrose esters or sucresters E473 in the above-cited amounts by weight. Advantageously, the mineral or cation zinc (II) is zinc oxide, lecithin is from sunflower and/or maize, the sucrester is E473 and the starch is a pregelatinized vegetable starch.

The solid composition of the present invention comprises or, alternatively, consists of an iodine salt, a lecithin (neither non-hydrolyzed nor enzymatically hydrolyzed) and sucrose esters or sucresters E473 in the above-cited amounts by weight. Advantageously, the mineral iodine is sodium iodate, lecithin is from sunflower and/or maize and the sucrester is E473 and the starch is a pregelatinized vegetable starch.

It is an object of the present invention a first method for preparing the solid compositions (semi-finished or raw material) of the present invention.

Said first method of the present invention is for preparing a solid composition comprising or, alternatively, consisting of a mineral, in the form of mineral salt, a lecithin, a sucrose ester or sucrester and, preferably, a vegetable starch, according to the above-cited embodiments.

Said first method does not contemplate the addition of solvents or water since it is a method in which all the individual components existing in the solid composition are mixed at solid state as powders or granules and in no case in aqueous solution or in the presence of solvents.

Said first method of the present invention comprises or, alternatively, consists of a series of processing steps through which the mineral salt selected from the group comprising magnesium (II) salts, preferably magnesium oxide or magnesium hydroxide; or calcium (II) salts, preferably tricalcium phosphate; or iron (III) salts, preferably iron pyrophosphate; or zinc salt, preferably zinc oxide; or iodine salts, preferably sodium iodate; or mixtures thereof is coated or enveloped or encapsulated with said lecithin and/or said sucrose ester or sucrester, depending on the adopted addition order, and with said vegetable starch, if any. The mineral salt at solid state is firstly contacted with said lecithin and then, secondly, with said sucrose ester or sucrester and/or said vegetable starch.

The mineral salt at solid state as powder or granules has a water content of less than 5%, preferably of less than 3% by weight.

The mineral salt containing the mineral magnesium (II) or calcium (II) or iron (III) or zinc (II) or iodine is used in an amount comprised from 50 to 90%, preferably from 60 to 80%, even more preferably from 70 to 75% by weight.

The lecithin being used has the characteristics as described above. The contact time between mineral salt and lecithin is comprised from 1 to 60 minutes, preferably from 10 to 50, even more preferably from 20 to 40 minutes.

The lecithin being used can be selected from a sunflower or maize or soya lecithin. The lecithin being used is a powdery lecithin having a water content comprised from 1.5 to 4.5%, preferably from 2 to 4%, even more preferably from 2.5 to 3.5%. Advantageously, the lecithin used in said first method is a powdery, sunflower lecithin E322.

In said first method for preparing the solid compositions of the present invention neither a hydrolyzed lecithin nor an enzymatically hydrolyzed lecithin is used.

Lecithin is in the solid compositions of the present invention in an amount comprised from 0.1 to 1%, preferably from 0.4 to 0.8%, even more preferably from 0.50 to 0.6% by weight.

Lecithin, when contacted with said mineral salt, arranges itself uniformly over said salt and, thus, over the mineral magnesium (II) or calcium (II) or iron (III) or zinc (II) or iodine as well.

The gelatinized or pregelatinized vegetable starch is selected from a rice starch or maize starch. Advantageously, the starch is rice starch. Advantageously, the rice starch is a gelatinized or pregelatinized native rice starch. The vegetable starch has the characteristics as described above.

The starch is in the solid compositions of the present invention in an amount comprised from 15 to 40%, preferably from 20 to 35%, even more preferably from 25 to 30% by weight.

The starch in the form of gelatinized or pregelatinized starch is advantageously more fluid and flowable and can be carefully dosed without causing errors or weight variations. Furthermore, it arranges itself in a more even and homogeneous manner. Finally, the pregelatinized starch enhances the bioavailability of the mineral salt and thus, of the mineral (cation contained within said mineral salt) as the obtained compound is better dissolved at temperatures comprised from 15 to 30° C. (pressure 1 atmosphere), preferably from 20 to 25° C., even more preferably from 18 to 23° C.

Following to said first preparing method, the solid compositions (semi-finished or raw material) as powder or granules or agglomerates of the present invention are obtained, which comprise or, alternatively, consist of mineral salts, a sucrose ester or sucrester, a lecithin (neither non-hydrolyzed nor enzymatically hydrolyzed) and, preferably, a pregelatinized vegetable starch, in the above-cited amounts by weight.

Particularly, by said first preparing method the solid compositions of the present invention are obtained, which comprise or, alternatively, consist of a mineral salt, a sunflower lecithin E322 (neither non-hydrolyzed nor enzymatically hydrolyzed), a sucrose ester or sucrester E473 and a pregelatinized rice starch, in the above-cited amounts by weight.

The Applicant found that in order to further enhance the bioavailability of the mineral salt and thus, of the mineral (cation contained within said mineral salt), the amount by weight of lecithin to be used in the process for preparing the solid compositions of the present invention has to be reduced as much as possible.

Advantageously, the non-hydrolyzed lecithin is in an amount of less than 1% by weight, relative to the weight of the solid composition; in an embodiment the non-hydrolyzed lecithin is in an amount of less than 0.8% by weight, preferably of less than 0.6% by weight.

Moreover, the Applicant found that in order to further enhance the bioavailability of the mineral salt and, thus, of the mineral (cation contained within said mineral salt), it is important to use a specific amount by weight of sucrose esters or sucresters in association with a reduced amount by weight of lecithin.

Advantageously, the sucrose ester or sucrester to lecithin ratio is comprised from 30:1 to 25:1. In an embodiment said ratio is comprised from 20:1 to 15:1.

It is an object of the present invention a second method for preparing the solid compositions of the present invention.

Said second method of the present invention is for preparing the solid compositions comprising or, alternatively, consisting of a mineral salt, sucrose esters or sucresters, a lecithin and a gelatinized or pregelatinized starch.

Said second method does not contemplate the addition of solvents or water since it is a method in which all the individual components existing in the solid composition are mixed at solid state as powders or granules and in no case in aqueous solution or in the presence of solvents.

Said second method of the present invention comprises or, alternatively, consists of a technology developed in order to create a coating or encapsulation around the mineral salt so that to improve the stability and bioavailability of the mineral salt and, thus, of the mineral (cation) therein contained as well.

Basically, said second method contemplates the formation of agglomerates or granules comprising the mineral salt, sucrose esters or sucresters, lecithin and a gelatinized or pregelatinized starch. All of these components have the characteristics as specified above.

The sucrose esters or sucresters and lecithin act by enhancing the absorption of the mineral salt and, accordingly, of the mineral (cation contained within said mineral salt). The admixture with lecithin and starch gives rise to the formation of "chimeric" agglomerates capable to protect and shield the cation contained within said mineral salt from the gastric acid.

The mineral salt containing the mineral (cation) is used in an amount comprised from 30 to 70%, preferably from 40 to 60%, even more preferably from 50 to 55% by weight.

The mineral salt being used has the characteristics as described above.

The processing time is comprised from 1 to 60 minutes, preferably from 10 to 50, even more preferably from 20 to 40 minutes.

The sucrose esters or sucresters are in an amount comprised from 10 to 30%, preferably from 15 to 25%, even more preferably from 16 to 20% by weight.

The lecithin being used is a maize or sunflower or soya lecithin. The lecithin being used is a powdery lecithin having a water content comprised from 1.5 to 4.5%, preferably from 2 to 4%, even more preferably from 2.5 to 3.5%.

Advantageously, the lecithin being used is a powdery sunflower lecithin. The lecithin being used has the characteristics as specified above. The lecithin being used is neither a hydrolyzed lecithin nor an enzymatically hydrolyzed lecithin.

Lecithin is in an amount comprised from 0.1 to 1%, preferably from 0.4 to 0.8% even more preferably from 0.5 to 0.6% by weight.

Lecithin arranges itself over the outer surface of granules or powders of the mineral salts when directly added to said mineral salts, or arranges itself over the outer surface of granules or powders comprising the mineral salt and sucrester, when added subsequently to sucrester.

Thereafter, a gelatinized or pregelatinized vegetable starch selected from a rice starch or maize starch is used.

Advantageously, the starch is a rice starch. Advantageously, the rice starch is a gelatinized or pregelatinized native rice starch. The starch (*Oryza sativa*) being used has the characteristics as specified above.

The starch is in the solid compositions of the present invention in an amount comprised from 15 to 40%, preferably from 20 to 35%, even more preferably from 25 to 30% by weight.

The gelatinized or pregelatinized starch is prepared according to the equipment and techniques known to the person skilled in the field. The gelatinization process of rice flour aims to modify its technological properties bringing about a molecular rearrangement of the starchy component: said changes allow to providing a greater plasticity and viscosity to the mixtures and improving several characteristics of the products in which they are used. The properties obtained by gelatinization and subsequent structural change of native starches contained in rice, allow the process to confer a faster hydration and a higher viscosity to flours. Moreover, the gelatinized starch strongly binds the water to the starchy matrix itself, thereby becoming less available. Accordingly, a longer storage time and a lower effect of chemical and enzymatic degradation phenomena are obtained. Pregelatinization is a physical technique (thus it does not contemplate the addition of other components) that modifies the starch properties and is based on cooking and subsequently drying an aqueous native starch suspension (namely "rough" flour). The pregelatinized starches display the pivotal functional property of adsorbing a high water amount, thus they are used as thickeners and gelling agents in several food formulations, especially when (and this is the case of rice or maize flours) the gluten protein fraction is absent. The cooking-extrusion (namely a short treatment at high temperatures and pressures) and drying carried out on cylinders represent the most common method for obtaining pregelatinization. Pregelatinized starch-based products show, among others, good storage characteristics. This is because the water being present is strongly structured and captured within the pregelatinized starch matrix, whereby becoming not more available for degradation reactions, while at the same time the thermal treatment abolished some enzymatic (lipase and lipoxygenase) activities which often promote oxidative rancidity phenomena in "rough" flours and products derived therefrom.

In an embodiment, lecithin is used in an amount comprised from 0.48 to 0.62% by weight, while sucrose esters or sucresters are used in an amount comprised from 16.5 to 18.5% by weight, relative to the weight of the final solid composition of the present invention. These combinations allow to enhancing the bioavailability of the cation contained within said mineral salt of interest.

Following to said second preparing method, the solid compositions (semi-finished or raw material) of the present invention are obtained, which comprise or, alternatively, consist of at least a mineral, in the form of mineral salt, sucrose esters or sucresters, a lecithin (neither non-hydrolyzed nor enzymatically hydrolyzed) and a pregelatinized vegetable starch, in the amounts by weight disclosed above.

Particularly, by said second preparing method, the solid compositions (semi-finished or raw material) of the present invention are obtained, which comprise or, alternatively, consist of magnesium (II), preferably magnesium oxide or magnesium hydroxide; or calcium (II), preferably tricalcium phosphate; or iron (III), preferably iron pyrophosphate; or zinc (II), preferably zinc oxide; or iodine, preferably sodium iodate mineral salts; or mixtures thereof, sucrose esters or sucresters E473, a sunflower lecithin (neither non-hydrolyzed nor enzymatically hydrolyzed) and a pregelatinized rice starch, in the amounts by weight disclosed above.

The solid compositions (semi-finished or raw material) of the present invention have a granulometry (that is understood as average granulometry measured by available equipment and techniques) comprised from 5 to 20 microns, preferably from 8 to 15 microns, even more preferably from 11 to 13 microns.

The solid compositions (semi-finished or raw material) of the present invention obtained through said first and second methods have a content of:
- magnesium (II), if present as magnesium oxide salt, comprised from 250 to 450 mg/g, preferably from 300 to 400 mg/g of composition,
- magnesium (II), if present as magnesium hydroxide salt, comprised from 150 to 300 mg/g, preferably from 200 to 250 mg/g of composition,
- calcium (II), if present as tricalcium phosphate salt, comprised from 250 to 450 mg/g, preferably from 300 to 400 mg/g of composition,
- iron (III), if present as iron pyrophosphate salt, comprised from 60 mg/g to 140 mg/g, preferably from 80 mg/g to 120 mg/g, even more preferably from 90 to 110 mg/g,
- zinc (II), if present as zinc oxide salt, comprised from 350 to 600 mg/g, preferably from 400 to 550 mg/g of composition,
- iodine, if present as sodium iodate salt, comprised from 5 to 20 mg/g, preferably from 8 to 15 mg/g of composition.

The solid compositions as granules or powder or agglomerates (semi-finished or raw materials), obtained by said first and second methods, are formulated with pharmacologically acceptable additives and excipients to obtain the formulations (final products) of the present invention in solid form such as powder or granules or agglomerates or solid, orally disintegrating powders.

It is an object of the present invention the orally disintegrating formulations (final products) as disclosed hereinafter.

The solid compositions (semi-finished or raw material) obtained as granules or powder or agglomerates are then formulated, by mixing, with sorbitol in an amount comprised from 40 to 90% by weight, preferably from 50 to 80% by weight, with maltodextrins in an amount comprised from 5 to 25% by weight, preferably from 9 to 20% by weight and citric acid in an amount comprised from 0.1 to 1% by weight and with other pharmacologically acceptable additives and excipients to obtain a final product (a supplement product, a medical device or a pharmaceutical composition) in the form of orally disintegrating granules or powder or agglomerates, preferably orally disintegrating granules, having a pharmaceutical form such as, for example a packet or stick.

All the solid formulations (final products) are used in conditions of complete or partial deficiency of minerals such as magnesium (II) or calcium (II) or iron (III) or zinc (II) or iodine, in particular they are for use in the treatment of disorders or diseases related to or derived from a deficiency of one or more of said minerals.

Furthermore, all the formulations (final products) object of the present invention are successfully used in the treatment of (i) a proper cognitive development, for example in adolescents; (ii) an adequate red blood cell and hemoglobin production; (iii) a reduction of tiredness and physical fatigue in an individual.

Advantageously, the solid formulations (final products) containing said solid compositions (semi-finished or raw material) prepared by the method disclosed above (said first and second methods) are such that the mineral salt and, thus, the mineral (magnesium (II) or calcium (II) or iron (III) or zinc (II) or iodine or mixtures thereof) is readily absorbable and bioavailable in an affective manner. The mineral is able to pass the gastric environment and, accordingly, can be directly absorbed at intestinal level thereby avoiding possible discomforts caused at gastric level.

Therefore, said formulations shown to be well-tolerated by the body.

Advantageously, the solid formulations of the present invention can be administered, even under fasting conditions, to all the subject categories and have a good palatability, a high long-term stability from the chemical-physical point of view and optimum organoleptic properties namely, when subjected to stability tests, the mineral salts did not bring about color, smell, flavor and/or taste changes.

It is an object of the present invention a liquid composition (semi-finished or raw material).

The liquid compositions (semi-finished or raw material) based on minerals of the present invention further comprise, besides one or more of the above-cited minerals in the form of mineral salt, a sucrester and a lecithin and, preferably, also a guar gum and water for obtaining liquid compositions (semi-finished or raw material).

The liquid compositions can be formulated with pharmacologically acceptable additives and excipients to obtain liquid formulations for oral use as suspension or syrup form.

The liquid formulations (final products) of the present invention are for oral use and suitable as supplement product, medical device or pharmaceutical composition (briefly the liquid compositions of the present invention, for the sake of brevity).

The liquid formulations (final products) of the present invention are suitable in conditions of complete or partial deficiency of minerals such as magnesium (II) or calcium (II) or iron (III) or zinc (II) or iodine, in particular they are for use in the treatment of disorders or diseases related to or derived from a deficiency of one or more of said minerals.

The liquid compositions (semi-finished or raw material) of the present invention comprise or, alternatively, consist of water, mineral salts, a lecithin as disclosed above, sucrose esters or sucresters as disclosed above and a guar gum.

All of these components have the characteristics and chemical-physical properties, as specified above.

The liquid compositions (semi-finished or raw material) of the present invention do not contain neither a hydrolyzed lecithin nor an enzymatically hydrolyzed lecithin.

The liquid compositions (semi-finished or raw material) of the present invention do not contain a diglycerol fatty acid ester.

The liquid compositions (semi-finished or raw material) of the present invention have a viscosity (measured under standard conditions and by known equipment and techniques) comprised from 1.01 to 1.15 g/ml, preferably from 1.02 to 1.12 g/ml, even more preferably from 1.03 to 1.10 g/ml.

The liquid compositions of the present invention comprise the minerals, as mineral salts, magnesium (II) or calcium (II) or iron (III) or zinc (II) or iodine; the mineral magnesium (II) can be magnesium oxide or magnesium hydroxide; the mineral calcium can be tricalcium phosphate E473; the mineral iron (III) can be iron pyrophosphate; the mineral zinc (II) can be zinc oxide and iodine can be sodium iodate.

The liquid compositions (semi-finished or raw material) of the present invention contain at least a mineral salt in an amount comprised from 1 to 10%, preferably from 2 to 8%, even more preferably from 4 to 6% by weight, relative to the weight of the liquid composition.

The liquid compositions (semi-finished or raw material) of the present invention further comprise sucrose esters or sucresters, having the characteristics as disclosed above.

Sucrose esters or sucresters E473 are in said liquid composition of the present invention in an amount comprised from 0.10 to 5%, preferably from 0.5 to 4%, even more preferably from 1 to 3% by weight, relative to the weight of the liquid composition.

The liquid compositions (semi-finished or raw material) of the present invention further comprise a lecithin, having the characteristics as disclosed above.

The lecithin E322 being used can be selected from a sunflower or maize or soya lecithin. Advantageously, the lecithin being used is a sunflower lecithin.

In an embodiment, the sunflower lecithin contains a glucose amount comprised from 20 to 60%, preferably from 30 to 50%, for example 45% by weight such as in the product Lecico Sun CG 450 from Lecico GmbH Company-Germany.

A sunflower lecithin usable in the context of the present invention can have the following composition by weight (chemical-physical analysis): sunflower lecithin from 40 to 50%, carbohydrates from 40 to 50% (for example, carbohydrates 42%), proteins from 6 to 10%, ashes from 3 to 8%, humidity from 2 to 5% and a glidant others from 0.5 to 1.5%.

Lecithin is in said liquid compositions in an amount comprised from 0.1 to 4%, preferably from 0.5 to 3.5%, even more preferably from 1.5 to 2.5% by weight, relative to the weight of the liquid composition.

The liquid compositions (semi-finished or raw material) of the present invention further comprise a guar gum.

The guar gum is in said liquid compositions in an amount comprised from 0.1 to 5%, preferably from 0.2 to 4%, even more preferably from 0.4 to 2% by weight, relative to the weight of the liquid composition.

In an embodiment, the guar gum is selected from those commercially available and has a viscosity (cPs, 2 hours) comprised from 3000-4500, preferably from 3500 to 4000; starch-free; with a content of acid-insoluble substances comprised from 5 to 9, preferably from 6 to 8, for example 7; with a R.U.A comprised from 2.5 to 4%, preferably from 3 to 3.5% and a granulometry comprised from 100 to 300, preferably from 150 to 250, for example 200.

It is an object of the present invention a process for preparing said liquid composition, which comprises or, alternatively, consists of a technology capable to yield a time-stable composition or emulsion or suspension depending on the operating conditions being used. The process provides the liquid compositions devoid of deposit (precipitates or agglomerates in suspension) and having an even and sustained concentration over the time.

In an embodiment, water is in an amount of 90%, or 92%, or 94% by weight. Water is kept under stirring at a temperature comprised from 15 to 45° C. (pressure 1 atmosphere), preferably from 20 to 35° C., even more preferably from 25 to 30° C.

Next, sucrose esters or sucresters, lecithin, guar gum and iron (III) salts (having the characteristics as disclosed above) are added in the amounts specified below. Sucrose esters or sucresters are in an amount comprised from 0.10 to 5%, preferably from 0.5 to 4%, even more preferably from 1 to 3% by weight, relative to the weight of the liquid composition.

Water and sucrose esters or sucresters form a clear solution/suspension at a temperature comprised from 15 to 45° C. (pressure 1 atmosphere), preferably from 20 to 35° C., even more preferably from 25 to 30° C.

The processing time is comprised from 1 to 60 minutes, preferably from 10 to 50 minutes, even more preferably from 20 to 40 minutes.

Lecithin (having the characteristics as disclosed above) is used in an amount comprised from 0.1 to 4%, preferably from 0.5 to 3.5%, even more preferably from 1.5 to 2.5% by weight, relative to the weight of the liquid composition.

Water, sucrose esters or sucresters and lecithin form a clear solution/suspension at a temperature comprised from 15 to 45° C. (pressure 1 atmosphere), preferably from 20 to 35° C., even more preferably from 25 to 30° C.

The guar gum (having the characteristics as disclosed above) is used in an amount comprised from 0.1 to 5%, preferably from 0.2 to 4%, even more preferably from 0.4 to 2% by weight, relative to the weight of the liquid composition.

Water, sucrose esters or sucresters, lecithin and guar gum form a clear solution/suspension at a temperature comprised from 15 to 45° C. (pressure 1 atmosphere), preferably from 20 to 35° C., even more preferably from 25 to 30° C.

Said iron salt (having the characteristics as disclosed above) is in an amount comprised from 1 to 10%, preferably from 2 to 8%, even more preferably from 4 to 6% by weight, relative to the weight of the liquid composition.

At the end of the processing step, an opalescent solution or a homogeneous suspension is obtained. The working temperature is comprised from 15 to 45° C. (pressure 1 atmosphere), preferably from 20 to 35° C., even more preferably from 25 to 30° C. The processing time is comprised from 1 to 60 minutes, preferably from 20 to 50 minutes, even more preferably from 30 to 40 minutes.

Next, the liquid composition is subjected to a thermal treatment, for example pasteurization. Basically, the liquid composition being at a temperature comprised from 20 to 25° C. is heated at a temperature of about 110° C. and then cooled down at a temperature of about 25-30° C. The thermal treatment step is carried out over a period comprised from 1 to 3 minutes.

Following to said process for preparing said liquid compositions, said liquid compositions (semi-finished or raw material) of the present invention are obtained, which comprise or, alternatively, consist of water, mineral salts, sucrose esters or sucresters, a lecithin (neither non-hydrolyzed nor enzymatically hydrolyzed) and a guar gum, in the amounts by weight specified above.

In particular, from said preparing process the liquid compositions of the present invention are obtained, which comprise or, alternatively, consist of water, magnesium (II) or calcium (II) or iron (III) or zinc (II) or iodine mineral salts, sucrose esters or sucresters E473, a sunflower lecithin (neither non-hydrolyzed nor enzymatically hydrolyzed) and a guar gum, in the amounts by weight specified above.

In an embodiment of the present invention, the solid compositions (semi-finished or raw material) obtained by said first and second methods as disclosed above, can be added of water together with guar gum for obtaining the liquid composition (semi-finished or raw material) of the present invention.

The liquid compositions, obtained by the above-cited methods, are then formulated with pharmacologically acceptable additives and excipients to form the liquid formulations (final products) of the present invention such as suspension or syrup, said liquid formulations being used in conditions of complete or partial deficiency of minerals such as magnesium (II) or calcium (II) or iron (III) or zinc (II) or iodine, in particular they are for use in the treatment of disorders or diseases related to or derived from a deficiency of one or more of said minerals.

Advantageously, the liquid formulations (final products) containing said liquid compositions (semi-finished or raw material) prepared by the methods described above are such that the mineral salt and, thus, the mineral (magnesium (II) or calcium (II) or iron (III) or zinc (II) or iodine) is readily absorbable and bioavailable in an effective manner.

Furthermore, said liquid formulations shown to be well-tolerated by the body.

Advantageously, the liquid formulations of the present invention can be administered, even under fasting conditions, to all the subject categories and have a good palatability, a high long-term stability from the chemical-physical point of view and optimum organoleptic properties namely, when subjected to stability tests, the mineral salts did not bring about to color, smell, flavor and/or taste changes.

The solid compositions for oral use of the present invention, obtained from said first and second methods, are raw materials at solid state (granules or agglomerates or powders) which are subsequently mixed with pharmaceutically acceptable additives and excipients to yield pharmaceutical forms for oral use such as orally disintegrating tablets, pastilles, capsules, packets, or powders.

The liquid composition for oral use of the present invention is mixed with pharmaceutically acceptable flavors, excipients and additives for obtaining a syrup or liquid suspension for oral use. Advantageously, the supplement product or medical device or pharmaceutical composition for oral use comprising the solid or liquid composition for oral use according to any of the above-cited embodiments, is successfully used in the treatment of disorders or diseases related to an iron deficiency in pediatric subjects, adolescents, athletes, men, women, pregnant women and elderly since they prevent anemia and are useful for increasing the hemoglobin and ferritin values. Said supplement product or medical device or said pharmaceutical composition, in solid form or liquid form, according to any of the above-cited embodiments is suitable for administration over a period comprised from 1 to 5 months, preferably from 2 to 4 months. Advantageously, said supplement product or medical device or said pharmaceutical composition, in solid form or orally disintegrating form or liquid form, for use in pediatric subjects, adolescents, athletes, men, women, pregnant women and elderly, is recommended at a dose comprised from 10 to 60 mg of mineral/day, preferably from 15 to 45 mg/day, even more preferably from 20 to 30 mg/day.

EXAMPLES

Example 1

Preparing a food supplement product comprising iron (III) pyrophosphate in packet form.

Firstly, a solid composition (semi-finished or raw material) containing iron (III) pyrophosphate 53.71% by weight, pregelatinized rice starch 28.57% by weight, sucresters E473 17.14% by weight and sunflower lecithin 0.58% by weight was prepared. Iron (III) pyrophosphate, sunflower lecithin and sucresters E473, in the above-cited amounts by weight, were mixed together over 30 minutes at a rate of 12.5 Hz to obtain a first mixture; next, the pregelatinized rice starch was added to the mixture obtained above and the whole was further mixed over 30 minutes at a rate of 12.5 Hz for obtaining a mixture which was subjected to a sieving step by a 0.7 mm sieve. Finally, the sieved mixture was further mixed for additional 30 minutes at a rate of 12.5 Hz.

Then, a food supplement product (final product) as 1.6 gram packet form comprising said solid composition was prepared.

Basically, the solid composition was mixed with the other ingredients of the supplement product through known equipment and methods. The ingredients of the supplement product are as follows:

Sweetener: xylitol; maltodextrins,
    solid composition containing iron (III) pyrophosphate, pregelatinized rice starch, sucresters E473 and sunflower lecithin (prepared above),
    L-ascorbic acid (vitamin C),
    nicotinamide (vitamin PP),
    flavors, acidity regulator: citric acid;
    calcium D-pantothenate (pantothenic acid),
    pyridoxine hydrochloride (vitamin B6),
    riboflavin (vitamin B2),
    thiamine mononitrate (vitamin B1),
    cyanocobalamin (vitamin B12).

The content of a supplement product in a 1.6 g packet is: iron (III) pyrophosphate (solid composition) 12 mg; vitamin C 48 mg; vitamin PP 16 mg; pantothenic acid 6 mg; vitamin B6 1.4 mg; vitamin B2 1.4 mg; vitamin B1 1.1 mg; folate 200 mcg; biotin 50 mcg; vitamin B12 2.5 mcg.

The iron (III) contained in said supplement product is able to pass intact through the gastric environment and be absorbed at intestinal level thereby avoiding possible discomforts caused at gastric level. The recommended dose is one packet per day, to be orally taken. The packet content is directly dissolved in the mouth.

The invention claimed is:

1. A solid composition for use in the treatment of disorders or diseases related to a mineral deficiency comprising:
a mineral salt selected from the group consisting of magnesium (II), calcium (II), iron (III), zinc (II), iodine mineral salts and mixtures thereof, wherein the mineral salt has a water content of less than 5%;
sucrose esters or sucresters E473; and
a lecithin;
wherein said lecithin is a non-hydrolyzed lecithin and is in an amount comprised from 0.1 to 1.5 percent by weight, relative to the weight of the composition, and
wherein said sucrose esters or sucresters E473 are in an amount of 10 to 30 percent by weight, relative to the weight of the composition.

2. The composition for use according to claim 1, wherein said sucrose esters or sucresters E473 and said lecithin are in a weight ratio comprised from 30:1 to 25:1.

3. The composition for use according to claim 1, wherein said composition further comprises a gelatinized or pregelatinized vegetable starch.

4. The composition for use according to claim 1, wherein said mineral salt is in an amount comprised from 30 to 70% by weight.

5. The composition for use according to claim 1, wherein said lecithin is a lecithin E322 and selected from the group comprising maize, sunflower or soya lecithin.

6. The composition for use according to claim 1, wherein said sucrose ester or sucrester and said lecithin are in the composition in a weight ratio comprised from 25:1 to 20:1.

7. The composition for use according to claim 3, wherein said gelatinized or pregelatinized vegetable starch is selected from rice starch or maize starch; said starch is in an amount comprised from 15 to 40% by weight.

8. The composition for use according to claim 1, wherein said solid composition for oral use has a granulometry comprised from 8 to 16 microns; a bulk density comprised from 0.3 to 0.8 g/ml and a content of mineral magnesium (II) or calcium (II) or iron (III) or zinc (II) or iodine comprised from 60 mg/g to 140 mg/g.

9. A method for preparing a solid composition according to claim 1, wherein said method comprises a step in which the mineral salt is mixed in the presence of non-hydrolyzed lecithin and sucrose esters or sucresters E473 to obtain said composition.

10. The method according to claim 9, wherein said composition further comprises a vegetable starch.

11. A method for the treatment of disorders or diseases related to or derived from a deficiency of minerals such as magnesium (II), calcium (II), iron (III), zinc (II), iodine or mixtures thereof in pediatric subjects, adolescents, athletes, men, women, pregnant women and elderly, wherein said method comprises administering a solid formulation comprising a composition according to claim 1.

12. The method according to claim 11, for reducing tiredness and physical fatigue.

13. The method according to claim 11, wherein said formulation is in orally disintegrating form.

14. The composition for use according to claim 3, wherein said gelatinized or pregelatinized vegetable starch is *Oryza sativa* rice starch.

15. The composition according to claim 4, wherein said mineral salt is in an amount comprised from 40 to 60% by weight.

16. The composition according to claim 4, wherein said magnesium (II) mineral salt is selected from magnesium oxide and magnesium hydroxide, said calcium (II) mineral salt is tricalcium phosphate E341, said iron (III) mineral salt is iron pyrophosphate, said zinc mineral salt is zinc (II) oxide and said iodine mineral salt is sodium iodate.

17. The composition for use according to claim 7, wherein said gelatinized or pregelatinized vegetable starch is in an amount comprised from 20 to 35% by weight.

18. The composition for use according to claim 6, wherein said sucrose ester or sucrester and said lecithin are in the composition in a weight ratio comprised from 20:1 to 15:1.

19. The composition for use according to claim 8, wherein said solid composition for oral use has a granulometry comprised from 10 to 14 microns.

20. The composition for use according to claim 8, wherein said solid composition for oral use has a bulk density comprised from 0.4 to 0.7 g/ml.

21. The composition for use according to claim 8, wherein said solid composition for oral use has a content of mineral magnesium (II) or calcium (II) or iron (III) or zinc (II) or iodine comprised from 80 mg/g to 120 mg/g.

22. The composition for use according to claim 8, wherein said solid composition for oral use has a content of mineral magnesium (II) or calcium (II) or iron (III) or zinc (II) or iodine comprised from 90 to 110 mg/g.

23. The method according to claim 13, wherein the solid formulation in orally disintegrating form further comprises sorbitol in an amount comprised from 40 to 90% by weight and other pharmacologically acceptable additives and excipients.

24. The method according to claim 23, wherein the solid formulation in orally disintegrating form comprises sorbitol in an amount comprised from 50 to 80% by weight.

25. The method according to claim 13, wherein the solid formulation in orally disintegrating form further comprises maltodextrins in an amount comprised from 5 to 25% by weight and other pharmacologically acceptable additives and excipients.

26. The method according to claim 25, wherein the solid formulation in orally disintegrating form comprises maltodextrins in an amount comprised from 9 to 20% by weight.

27. The method according to claim 13, wherein the solid formulation in orally disintegrating form further comprises citric acid in an amount comprised from 0.1 to 1% by weight and other pharmacologically acceptable additives and excipients.

28. The composition according to claim 1, wherein said sucrose esters or sucresters E473 are in an amount comprised from 15 to 25% by weight.

29. A solid composition for use in the treatment of disorders or diseases related to a mineral deficiency comprising:
a mineral salt selected from the group consisting of magnesium (II), calcium (II), iron (III), zinc (II), iodine mineral salts and mixtures thereof, wherein the mineral salt is present in an amount from 30 to 70% by weight, relative to the weight of the composition;

sucrose esters or sucresters E473 in an amount from 10 to 30% by weight, relative to the weight of the composition;

a non-hydrolyzed lecithin in an amount from 0.1 to 1.5% by weight, relative to the weight of the composition; and a gelatinized or pregelatinized vegetable starch present in an amount from 15 to 40% by weight, relative to the weight of the composition.

* * * * *